United States Patent [19]

Morita et al.

[11] Patent Number: 5,174,160
[45] Date of Patent: Dec. 29, 1992

[54] METHOD OF DIAGNOSING ELECTRIC WIRES AND CABLES FOR DETERIORATION OF THEIR POLYMER-INSULATION AND A MEASURING APPARATUS USED THEREFOR

[75] Inventors: Yousuke Morita; Toshiaki Yagi; Waichiro Kawakami, all of Gunma; Seiji Kamimura, Ibaraki; Hideki Yagyu, Ibaraki; Osamu Mochizuki, Ibaraki; Takao Onishi, Ibaraki, all of Japan

[73] Assignees: Japan Atomic Energy Research Institute; Hitachi Cable Ltd., both of Tokyo, Japan

[21] Appl. No.: 584,049

[22] Filed: Sep. 18, 1990

[30] Foreign Application Priority Data

Sep. 19, 1989 [JP] Japan .................. 1-242530

[51] Int. Cl.⁵ .............................................. G01N 3/22
[52] U.S. Cl. ........................................ 73/847; 73/866
[58] Field of Search ............ 73/847, 848, 866, 150 R, 73/150 A

[56] References Cited

U.S. PATENT DOCUMENTS

| | | | |
|---|---|---|---|
| 2,980,851 | 4/1961 | Henning | 73/848 X |
| 3,683,682 | 8/1972 | Jochmann | 73/842 |
| 3,724,265 | 4/1973 | La Valle | 73/827 |
| 4,055,992 | 11/1977 | Pizarello | 73/791 |
| 4,943,757 | 7/1990 | Richter et al. | 318/256 X |

FOREIGN PATENT DOCUMENTS

| | | | |
|---|---|---|---|
| 69347 | 1/1983 | European Pat. Off. | 73/847 |
| 1193512 | 11/1985 | U.S.S.R. | 73/847 |

OTHER PUBLICATIONS

"Determination of Elastic Limit in Twisting"; *Ind. Lab.* (*USA*), vol. 36, No. 10, Oct. 1970; I. N. Kidin et al; pp. 1575-1578.

*Primary Examiner*—Tom Noland
*Attorney, Agent, or Firm*—Banner, Birch, McKie & Beckett

[57] ABSTRACT

This invention relates to a method or apparatus by which comparatively low-voltage electric wires and cables laid at power stations and other locations can be diagnosed for deterioration of their polymer-insulation in a non-destructive way. The method or apparatus comprises applying a torsional force to the electric wire or cable, detecting the resulting repulsion as a torque, and estimating the degree of deterioration of the polymer-insulation in the electric wire or cable on the basis of the detected value of torque.

16 Claims, 4 Drawing Sheets

METHOD OF DIAGNOSING ELECTRIC WIRES AND CABLES FOR DETERIORATION OF THEIR POLYMER-INSULATION AND A MEASURING APPARATUS USED THEREFOR

BACKGROUND OF THE INVENTION:

This invention relates to a method by which comparatively low-voltage electric wires and cables laid at power stations and other locations can be diagnosed for deterioration of their polymer-insulation in a non-destructive way. The invention also relates to a measuring apparatus used for implementing that method.

Many kinds of electric wires and cables are installed in nuclear power plants and they are more or less exposed to a radiation and/or thermal atmosphere. Including those which are used in such environments, electric wires and cables generally experience electrical or mechanical deterioration during prolonged use on account of various factors and must eventually be replaced.

The principal reason for the deterioration of polymer-insulators (consist of mainly a sheath and a insulator) in electric wires and cables would be oxidation and the resulting hardening (or softening in a rare case) causes a drop in the mechanical or electrical characteristics of electric wires and cables to such an extent that they will no longer perform in a normal and safe way. Hence, in order to enhance the safety of power plants and other facilities where electric wires and cables are installed so as to prevent the occurrence of accidents, it is very important that any deterioration of the electric wires and cables used be detected by a simple and yet reliable method. Accordingly, the development of such a method has been strongly desired.

In response to this need, active R&D efforts have long been made on a so-called "live-line diagnostic method" which is a non-destructive method for checking any deterioration in the polymer-insulation of live high-voltage cables. In addition to the already popular insulation resistance, dielectric constant and d.c. leakage current methods, various other techniques have recently been proposed, including a reverse absorption current method, a residual voltage method and a potential attenuation method. Today, these electrical non-destructive diagnostic methods also have been studied to make it feasible to check the deterioration of electric wires and cables with fairly high reliability.

High-voltage cables have a shield layer around the cable structure which can be utilized to perform diagnosis for deterioration by non-destructive electrical methods. Thus, the conventional methods for checking the degree of deterioration in high-voltage cables are not suitable for application to comparatively low-voltage wires and cables which do not have a shield layer.

Under these circumstances, the deterioration of low-voltage electric wires and cables has been checked by skilled personnel through visual inspection or by destroying removed parts so as to measure the loss in the electrical and mechanical characteristics, in particular, the residual elongation of their polymer-insulation materials. The visual inspection method is most commonly used to check the degree of deterioration of the polymer-insulation in low-voltage electric wires and cables which account for nearly half of the wires and cables used in power plants but this technique requires considerable skill on the part of inspectors and, furthermore, even skilled inspectors are subject to personal errors and will experience great difficulties in accomplishing accurate and reliable checking of the deterioration of the polymer-insulation. The second approach which involves destruction of removed parts not only lacks convenience but also requires substantial labor and time.

SUMMARY OF THE INVENTION

An object, therefore, of the present invention is to provide a novel method by which low-voltage electric wires and cables which account for nearly half of the wires and cables used in power plants can be diagnosed for deterioration of polymer-insulation in a non-destructive, reliable and accurate way while those wires and cables remain live on the inspection site in the same way as the aforementioned high-voltage electric cables.

Another object of the present invention is to provide an apparatus that is suitable for use in implementing that method.

The first object of the present invention can be attained by a method which comprises the steps of applying a torsional force to an electric wire or cable of interest, detecting the resulting repulsion as a torque, and estimating the degree of deterioration in said electric wire or cable of interest on the basis of the detected value of torque.

The second object of the present invention can be attained by an apparatus which comprises: a drive motor serving as a rotational drive source; an eccentric plate which is rotated by said motor; a rotating/rocking plate which is coupled to the eccentric portion of said eccentric plate by a connecting rod and the amount of rocking of which is adjustable by controlling the position of said eccentric portion; a rotational shaft which is coupled to said rocking plate and which rocks and rotates together with said rocking plate; a holder means which is secured at one end to said rotational shaft for transmitting the rocking motion of said rotational shaft to a test piece; and a torque cell for detecting the repulsive torque of said test piece which is retained by another holder means on the side opposite and first-mentioned holder means and which is provided with a torsional force by the rotating and rocking motion of said rotational shaft.

In a preferred embodiment of the present invention, a microstrain gage is attached to an electric wire or cable of interest and small static or cyclic torsional force is applied to said wire or cable, with the resulting strain or the phase difference between the torsional force applied and the strain being detected to evaluate the degree of deterioration of the polymer-insulation in said wire or cable.

Figure 1:
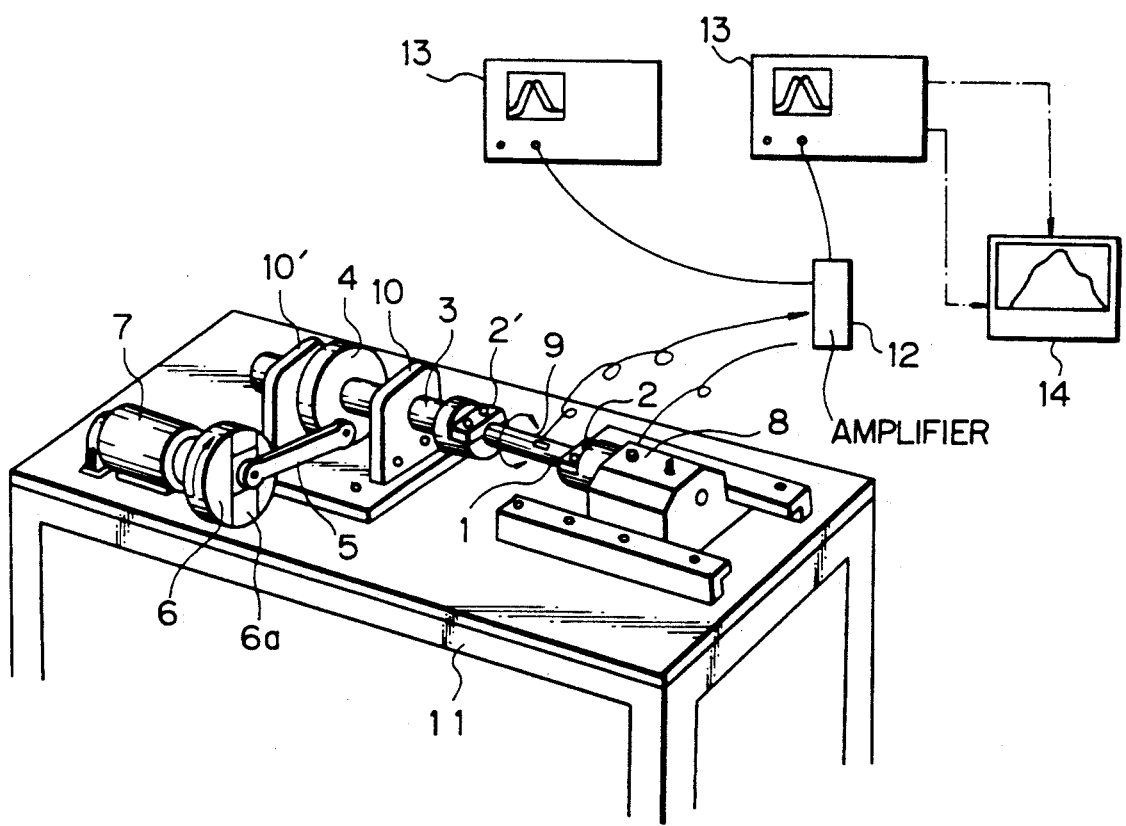
FIG. 1 is a perspective view showing a specific example of the apparatus used to implement the method of the present invention.

DETAILED DESCRIPTION OF THE INVENTION:

When the polymer-insulator in an electric wire or cable deteriorates upon exposure to heat or radiation, it hardens (or softens in a very rare case) to experience a change in its modulus of elasticity. A cyclic torsional force is applied to a wire or cable as a test piece and the resulting repulsive torque is converted to an electric signal, which is compared with a known value of torque for a control the degree of deterioration of the polymer-insulators in which is already known. By this procedure, the degree of deterioration in the test piece can be estimated in a non-destructive, easy and reliable way while it remains live.

According to the present invention, the degree of deterioration of the polymer-insulators in an electric wire or cable can also be estimated by measuring the strain resulting from the application of a torsional force or the phase difference between that torsional force and the resulting strain.

EXAMPLES

The following examples are provided for the purpose of further illustrating the present invention but are in no way to be taken as limiting.

EXAMPLE 1

A three-conductor 600 V (low voltage) crosslinked polyethylene (hereinafter abbreviated as XLPE) insulated polyvinyl chloride (hereinafter abbreviated as PVC) sheathed cable (hereinafter abbreviated as a "CV cable") was used as a specimen in the following test. The CV cable is most extensively used in power plants.

Polyethylene having the same composition as the one which was used in cable installed in an actual power plant was extrusion-coated over stranded wires (5.5 mm$^2$) and cross-linked to prepare a single cable conductor. Three such cable conductors were stranded with jute being provided in the interstices and a sheath of polyvinyl chloride having the same composition as the one which was used in cables installed in an actual power plant was extrusion-coated over the strand, whereby a sample of three-conductor, low-voltage CV cable was fabricated.

Simulating an actual environment, the so fabricated samples were placed in a thermostatic bath at 50° C. and irradiated with γ-rays at a dose rate of $1 \times 10^5$ R/h in an oxygen atmosphere to cause thermal and radiation deterioration. After irradiation for a given total dose, four of the samples were taken out and subjected to various measurements.

A tensile test was conducted with each cable sample being separated into the insulator and the sheath. The insulator XLPE was freed of the conductors and the resulting tube was stretched at a speed of 200 mm/min, whereas the sheath PVC was punched out to form a dumbbell which was stretched at the same speed of 200 mm/min.

The torque developing in the cables was measured under the following conditions:
Cycle speed: 0.5 Hz
Cyclic torsional angle: ±5°
Jaw distance on chuck: 50 mm.

The torque developing on the cable sheath was measured under the same conditions as described above after the insulator and the interstitial jute (the combination will hereinafter be referred to as the "core") was removed from the cable. The torque on the core was calculated by subtracting the value of torque on the sheath from the value for the cable.

Figure 2:
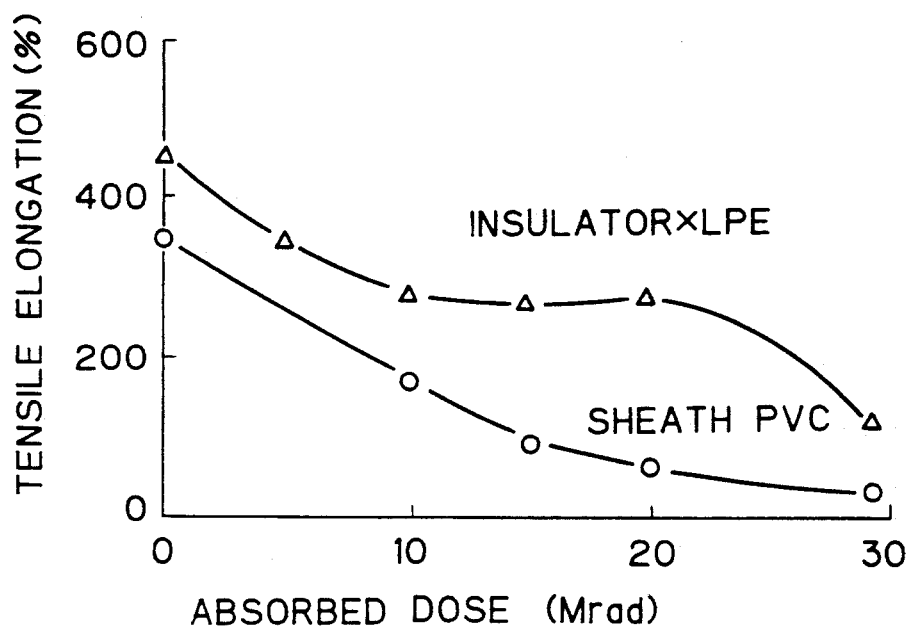
FIG. 2 is a graph showing the relationship between the absorbed dose and tensile elongation of the cable sheath and the cable insulator.
Figure 3:
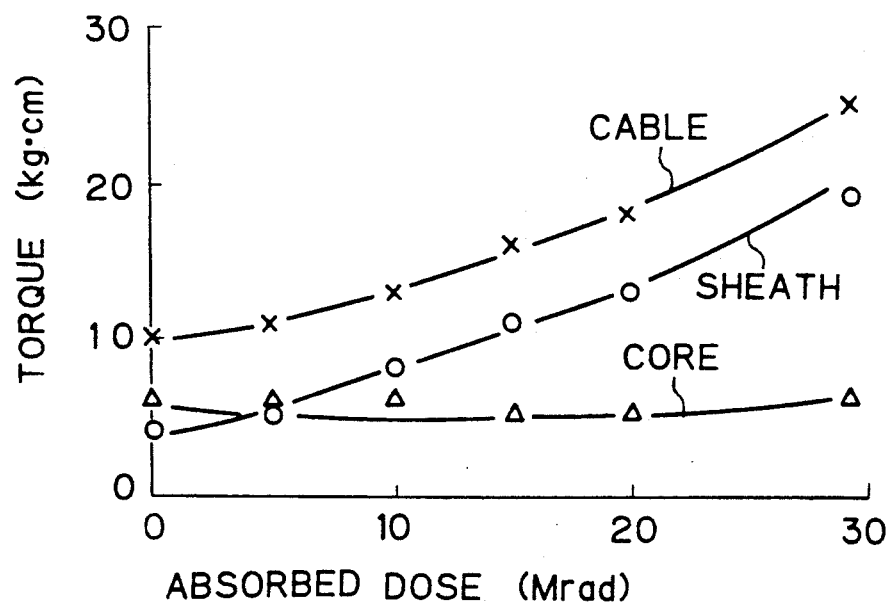
FIG. 3 is a graph showing the relationship between the absorbed dose and the increase in torque.
Figure 4:
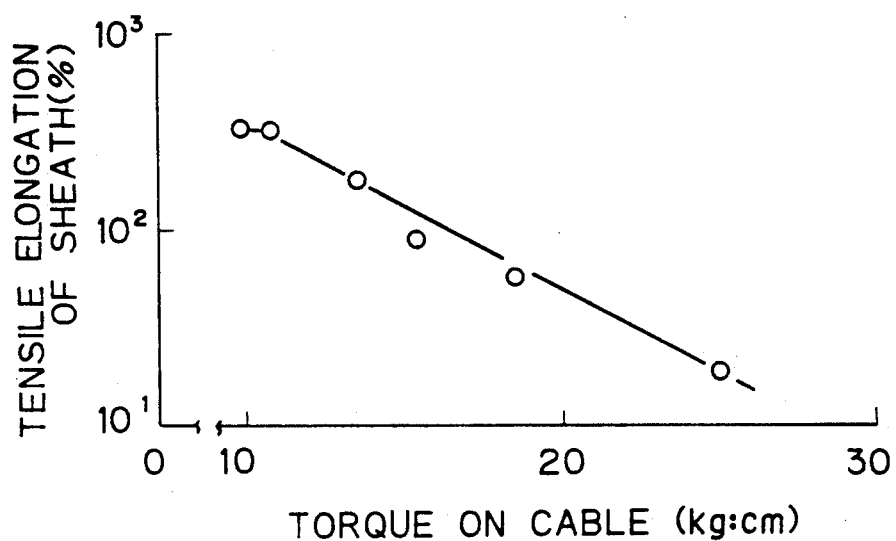
FIG. 4 is a graph showing the relationship between the value of torque on a cable and the elongation of the cable sheath as a measure of the deterioration in the cable.

FIG. 2 shows graphically the profile of simultaneous thermal and radiation deterioration of the insulator XLPE and sheath PVC in terms of the change in their mechanical characteristics, especially tensile elongation (TE), vs. absorbed dose. FIG. 3 shows the value of repulsive torque vs. absorbed dose. FIG. 4 shows the relationship between the elongation of the sheath and the value of repulsive torque on the cable.

As one can see from FIG. 2, the tensile elongation of the sheath as the outermost layer of the cable decreased more greatly due to simultaneous thermal and radiation deterioration than the insulator and the decrease in the tensile elongation of the cable is determined by the sheath. It can also be seen from FIG. 3 that the dose-dependency of the torque on the cable is chiefly governed by the torque on the sheath and that the internal core is hardly influenced by the absorbed dose. Further, it is clear from FIG. 4 that the increase in the repulsive torque on the cable due to simultaneous thermal and radiation deterioration correlates well to the decrease in the tensile elongation of the sheath. These facts show that by measuring the repulsive torque on the cable, the tensile elongation of the sheath which determines the life of the cable can be known in a non-destructive way, which contributes to accurate estimation of the degree of deterioration in the cable.

Thus, with data on deterioration being preliminarily obtained for an insulator of the same formulation as the one used in actual wires and cables, one may apply a torsional force to a live electric wire or cable under test and compare the value of the resulting torque with the known data to correctly estimate the degree of deterioration in the insulator in said electric wire or cable.

FIG. 1 is a perspective view showing a specific example of the apparatus that may be used to diagnose an electric wire or cable for the deterioration of its polymer-insulation by the method described above.

Shown by 1 in FIG. 1 is a test piece which, in actual measurements, is a live electric wire or cable that is fixed in a position for measurement. For the sake of clarity, an electric wire of a short length is shown as a test piece in FIG. 1 but in an actual apparatus, holder means 2 and 2' are desirably adapted in such a way that an electric wire of a long length can be held in position, with the middle part of the wire being exposed to allow for the necessary length for torque measurement as shown in FIG. 1.

Brackets 10 and 10' are fixed to stand in a vertical position on a table 11 so that they support a rotational shaft 3 and a rocking plate 4 fixed to said shaft 3 in such a way that they can rotate and rock.

Shown by 7 is a speed reducer that allows a fast running drive motor (not shown) to rotate at a slower speed. The speed reducer 7 has secured thereto an eccentric plate 6 that is caused to rotate by said reducer in the direction indicated by the arrow. The eccentric plate 6 has an eccentricity adjusting mechanism 6a which is coupled to the rocking plate 4 by a connecting rod as shown in FIG. 1. The eccentricity adjusting mechanism 6a has an eccentric portion that can be moved as appropriate so that the rocking plate 4 will rock in alternate directions, with the amplitude of rocking being determined by the position of the eccentric portion, since it is coupled to the eccentric plate 6 by the connecting rod 5. As a consequence, the rotational shaft 3 rocks and rotates in such a way that the holder means 2' fixed to its end will rock in the directions indicated by the two-headed arrow.

The other holder means 2 which makes a pair with the holder means 2', with a reference distance being allowed for torque measurement, is secured to a torque cell 8. When the holder means 2' rocks and rotates as described above, a torsional force is applied to the test piece 1 retained between the two holder means, and the resulting torque on the test piece 1 is transmitted to the torque cell 8 by way of the holder means 2 so as to enable its measurement.

The thus measured value of torque may be recorded or read by means of a conventional device. FIG. 1 shows the case where the torque value (which may include the value of measurement with a strain gage) is converted to an electric signal and amplified with an amplifier 12 to be either displayed on an oscilloscope 13 or recorded on an X-Y recorder 14. However, this is not necessarily the case and various other methods can be employed including, for example, storing the data in a digital recorder or a personal computer.

The apparatus described above may be further reduced in size to realize a compact and handy type which can be freely brought into the site of measurement, where it is conveniently installed on an electric wire or cable of interest and used to diagnose it for any deterioration of its insulation while it remains live.

The foregoing example relates to the diagnosis of electric wires and cables installed in a nuclear power plant but this is not necessarily the case of the applicability of the present invention. There is no exaggeration that changes in the modulus of elasticity will inevitably occur in organic materials upon exposure to heat or radiation and, needless to say, the method and apparatus of the present invention for detecting such a change in the modulus of elasticity as the value of torque can be applied not only to the CV cable described above but also to many other cables.

EXAMPLE 2

This example relates to another method of the present invention in which the degree of deterioration in an electric wire or cable is checked on the basis of the strain developing upon exertion of a torsional force or the phase difference between the torsional force applied and the resulting strain.

This method can be implemented by an apparatus which is basically of the same type as shown in FIG. 1. A strain gage 9 is attached to the test piece 1 with an adhesive or by other suitable method. A torsional force is applied to the test piece 1 and the resulting strain or the phase difference between the applied torsional force and the resulting strain as detected with the strain gage 9 is read on the oscilloscope 13 or some other suitable instrument.

A 350Ω gage for two-axial torque (Model KFC-2-350-D2-11 of Kyowa Electric Instruments Co., Ltd.) was used as the strain gage 9 and attached to the test piece 1 with an adhesive. A digital gage applicable for strains in the range of $\pm 1000 - \pm 6400 \times 10^{-6}$ (WGA 700A of Kyowa Electric Instruments Co., Ltd.) was connected to the strain gage 9 and strain measurements were conducted under the following conditions:

Cycle speed: 0.5 Hz
Cyclic torsional angle: ±1°
Jaw distance on chuck: 50 mm.

Figure 5:
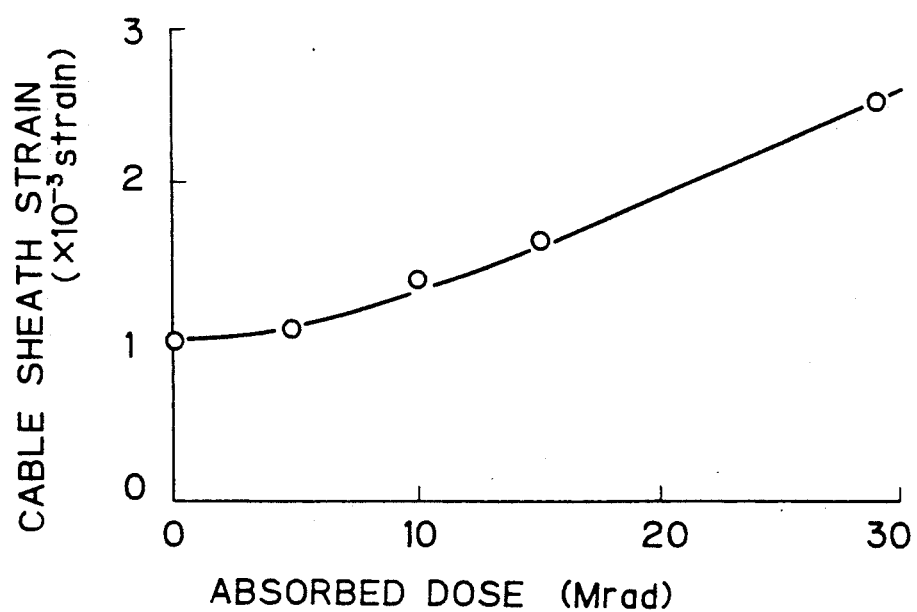
FIG. 5 is a graph showing the relationship between the absorbed dose and the strain in the cable sheath.
Figure 6:
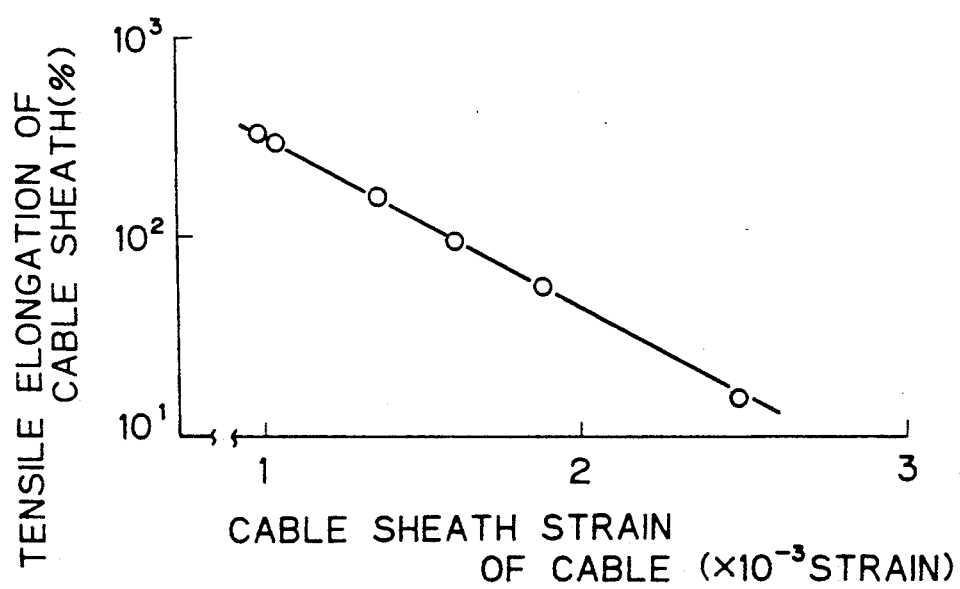
FIG. 6 is a graph showing the relationship between the strain in the cable sheath and the elongation of the sheath as a measure of the deterioration in the cable.

FIG. 5 shows the relationship between the absorbed dose and the strain developing on the cable sheath. It can be seen from FIG. 5 that the strain on the cable sheath varies with absorbed dose. FIG. 6 shows the relationship between the tensile elongation of the cable sheath and the strain. It can be seen from FIG. 6 that the strain on the cable sheath is correlated to its tensile elongation. Thus, a measurement of the strain developing on the cable sheath enables a non-destructive estimation of its elongation which determines the life of the cable.

As will be understood from the foregoing description, the method and apparatus of the present invention permit comparatively low-voltage electric wires and cables to be simply and correctly checked and diagnosed for deterioration even in a live state although this has been difficult or impossible to accomplish by the prior art except by visual inspection. Accordingly, the present invention will offer great benefits to the industry.

What is claimed is:

1. A method of estimating the degree of deterioration of an electric wire or cable having a polymer insulation comprising the steps of:
    applying a torsional force to said electric wire or cable;
    detecting the resulting repulsion as a torque; and
    estimating the degree of deterioration in said electric wire or cable on the basis of the detected value of torque.

2. The method according to claim 1, wherein said electric wire or cable is a low-voltage electric wire or cable.

3. The method according to claim 1, wherein said polymer insulation comprises polyethylene.

4. The method according to claim 1, wherein said polymer insulation comprises crosslinked polyethylene.

5. The method according to claim 1, wherein said polymer insulation comprises polyvinyl chloride.

6. The method according to claim 1, wherein the polymer insulation comprises a sheath and an insulator.

7. The method according to claim 6, wherein said sheath comprises polyvinyl chloride and said insulator comprises crosslinked polyethylene.

8. The method according to claim 1, wherein said step of estimating comprises comparing the detected value of torque with a known torque value.

9. A method of estimating the degree of deterioration of a polymer insulation in an electric wire or cable, the method comprising the steps of:
    holding said electric wire or cable in at least first and second points along a longitudinal axis thereof;
    applying a substantially non-destructive torsional force to said electric wire or cable at the first holding point;
    detecting the resulting repulsion against the torsional force as a torque at the second holding point; and
    estimating the degree of deterioration of said polymer insulation from the detected value of torque.

10. The method according to claim 9, wherein said electric wire or cable is a low-voltage electric wire or cable.

11. The method according to claim 9, wherein said polymer insulation comprises polyethylene.

12. The method according to claim 9, wherein said polymer comprises crosslinked polyethylene.

13. The method according to claim 9, wherein said polymer insulation comprises polyvinyl chloride.

14. The method according to claim 9, wherein the polymer insulation comprises a sheath and an insulator.

15. The method according to claim 14, wherein said sheath comprises polyvinyl chloride and said insulator comprises crosslinked polyethylene.

16. The method according to claim 9, wherein said step of estimating comprises comparing the detected torque with a known torque.

* * * * *